US00PP13775P29

(12) United States Plant Patent
McDonald

(10) Patent No.: US PP13,775 P2
(45) Date of Patent: May 6, 2003

(54) ARGYRANTHEMUM PLANT NAMED 'SUPAROSA'

(75) Inventor: Daniel Bede McDonald, Seven Hills (AU)

(73) Assignee: Nuflora International Pty. Ltd., Sydney (AU)

( * ) Notice: Subject to any disclaimer, the term of this patent is extended or adjusted under 35 U.S.C. 154(b) by 0 days.

(21) Appl. No.: 10/142,849

(22) Filed: May 10, 2002

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Argyranthemum plant named 'Suparosa', characterized by its compact, mounded, upright and outwardly spreading plant habit; freely branching habit, dense and bushy plants; freely flowering habit with numerous inflorescences per plant; single daisy inflorescence form with red purple-colored ray florets that fade to light pink with subsequent development; and red-colored immature disc florets that become bright yellow with subsequent development.

1 Drawing Sheet

BOTANICAL CLASSIFICATION/CULTIVAR DENOMINATION

*Argyranthemum frutescens* cultivar Suparosa.

BACKGROUND OF THE INVENTION

The present invention relates to a new and distinct cultivar of Argyranthemum plant, botanically known as *Argyranthemum frutescens* and hereinafter referred to by the cultivar name 'Suparosa'.

The new Argyranthemum is a product of a planned breeding program conducted by the Inventor in Cobbitty, New South Wales, Australia. The objective of the program is to create and develop new compact Argyranthemum cultivars with numerous inflorescences, interesting inflorescence form, and attractive ray floret coloration.

The new Argyranthemum originated from a cross-pollination by the Inventor of a proprietary selection of *Argyranthemum frutescens* identified as code number X96.143.1, not patented, as the female, or seed, parent, with a proprietary selection of *Argyranthemum frutescens* identified as code number X97.387.1, not patented, as the male, or pollen, parent. The new Argyranthemum was discovered and selected by the Inventor as a plant within the progeny of the stated cross-pollination in a controlled environment in Cobbitty, New South Wales, Australia in October, 1999. The selection of the new Argyranthemum was based on its single daisy inflorescence form and pink-colored ray florets.

Asexual reproduction of the new Argyranthemum by terminal cuttings taken in a controlled environment in Cobbitty, New South Wales, Australia since October, 1999, has shown that the unique features of this new Argyranthemum are stable and reproduced true to type in successive generations.

SUMMARY OF THE INVENTION

The new Argyranthemum has not been observed under all possible environmental conditions. The phenotype may vary somewhat with variations in environment such as temperature and light intensity without, however, any variance in genotype.

The following characteristics have been repeatedly observed and are determined to be basic characteristics of 'Suparosa' and distinguish the new Argyranthemum as a new and distinct cultivar:

1. Compact, mounded, upright and outwardly spreading plant habit.
2. Freely branching habit, dense and bushy plants.
3. Freely flowering habit with numerous inflorescences per plant.
4. Single daisy inflorescence form with red purple-colored ray florets that fade to light pink with subsequent development.
5. Red-colored immature disc florets that become bright yellow with subsequent development.

Plants of the new Argyranthemum are more compact and have lighter colored ray florets than plants of the female parent selection. Plants of the new Argyranthemum differ primarily from plants of the male parent selection in ray floret coloration.

Plants of the new Argyranthemum can be compared to plants of the cultivar Cobsing, disclosed in U.S. Plant patent application Ser. No. 09/996,381. In side-by-side comparisons conducted in Encinitas, Calif., plants of the new Argyranthemum differed from plants of the cultivar Cobsing in the following characteristics:

1. Inflorescences of plants of the new Argyranthemum were held higher above the foliage than inflorescences of plants of the cultivar Cobsing.
2. Plants of the new Argyranthemum had darker colored ray florets than plants of the cultivar Cobsing.
3. Immature disc florets of plants of the new Argyranthemum were red in color whereas immature disc florets of plants of the cultivar Cobsing were bright yellow in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Argyranthemum.

The photograph at the top of the sheet comprises a side perspective view of three typical flowering plants of 'Suparosa' grown in a 22-cm container.

The photograph at the bottom of the sheet comprises a close-up view of typical leaves, an inflorescence bud, a developing inflorescence, lower and upper surfaces of fully opened inflorescences of 'Suparosa', and an inflorescence with faded ray florets.

DETAILED BOTANICAL DESCRIPTION

The aforementioned photographs, following observations and averaged measurements describe plants grown in Encinitas, Calif., in an outdoor nursery under full sunlight during late winter and early spring with day temperatures averaging 15° C. and night temperatures averaging 10° C. Plants were grown for about 14 weeks in 22-cm containers with three plants per container. Plants were pinched one time about five weeks after planting. Color references are made to The Royal Horticultural Society Colour Chart, 1995 Edition, except where general terms of ordinary dictionary significance are used.

Botanical classification: *Argyranthemum frutescens* cultivar Suparosa.

Parentage:

*Female or seed parent.*—Proprietary selection of *Argyranthemum frutescens* identified as code number X96.143.1, not patented.

*Male or pollen parent.*—Proprietary selection of *Argyranthemum frutescens* identified as code number X97.387.1, not patented.

Propagation:

*Type.*—Terminal vegetative cuttings.

*Time to initiate roots.*—About 10 days at 20° C.

*Time to produce a rooted cutting.*—About 21 days at 20° C.

*Root description.*—Fibrous, fine and freely branching; white in color.

Plant description:

*General appearance.*—Inverted triangle; compact, mounded, upright and outwardly spreading plant form with dense foliage and inflorescences held above the foliage on long peduncles. Vigorous growth habit.

*Plant height.*—About 36 cm.

*Plant width, per plant.*—About 28 cm.

*Lateral branch description.*—Quantity per plant: About 16 primary lateral branches; each with about 12 secondary lateral branches. Length, soil level to base of peduncle: About 16 cm. Diameter: About 5 mm. Internode length: About 2.5 cm. Aspect: Upright and outwardly spreading. Texture: Smooth, glabrous. Color: 144C.

*Foliage description.*—Arrangement: Alternate, simple. Length: About 6.5 cm. Width: About 3.5 cm. Shape: Pinnatifid, deeply and finely incised. Apex: Acute. Base: Attenuate. Margin: Entire; deeply and finely incised. Texture, upper and lower surfaces: Smooth, glabrous. Venation pattern: Pinnate. Petiole length: About 2 cm. Petiole diameter: About 4 mm. Petiole texture, upper and lower surfaces: Smooth, glabrous. Color: Young foliage, upper surface: 137A. Young foliage, lower surface: 137C. Fully expanded foliage, upper surface: 137C. Fully expanded foliage, lower surface: 147B. Venation, upper surface: 137D. Venation, lower surface: 147B. Petiole, upper surface: 147C. Petiole, lower surface: 147D.

Inflorescence description:

*Appearance.*—Single daisy composite inflorescence form with ligulate ray florets. Disc and ray florets develop acropetally on a capitulum. Inflorescences held upright on terminal and axillary peduncles. Inflorescences upright and perpendicular to the peduncles. Inflorescences persistent. Inflorescences faintly fragrant; pungent.

*Flowering response.*—Under natural conditions, plant flower from spring to early fall in Southern California; plants flower continuous during this period.

*Inflorescence longevity.*—Inflorescences last about five to seven days on the plant.

*Quantity of inflorescences.*—Freely flowering, about seven buds and opened inflorescences per lateral branch.

*Inflorescence size.*—Diameter: About 4 cm. Depth (height): About 1 cm. Diameter of disc: About 1.3 mm.

*Inflorescence buds, at stage of showing color.*—Height: About 1 cm. Diameter: About 6 mm. Shape: Ovoid. Color: 63B.

*Ray florets.*—Quantity per inflorescence: About 22 arranged in a single whorl. Shape: Ligulate. Length: About 1.8 cm. Width: About 6 mm. Apex: Rounded. Base: Acute. Margin: Entire. Texture, upper and lower surfaces: Smooth, velvety. Aspect: Initially upright; when mature, about 90° from vertical; slightly reflexing with subsequent development. Color: When opening, upper surface: 68A; towards base, 155D, forming a ring around the disc. When opening, lower surface: 68D. Fully opened, upper surface: 155D overlain with 70C; towards apex, 155D; towards base, 155D, forming a ring around the disc. Color fading to 155D faintly overlain with 70C with subsequent development. Fully opened, lower surface: 75D.

*Disc florets.*—Arrangement: Massed at the center of the inflorescence. Quantity per inflorescence: About 200. Shape: Tubular, five-parted at apex; apex, acute; base, fused. Length: About 5 mm. Diameter, apex: About 1 mm. Diameter, base: Less than 1 mm. Color: Immature, apex: 179A. Immature, mid-section and base: 157A. Mature, apex: 17A. Mature, mid-section: 16C. Mature, base: 157A.

*Involucral bracts (phyllaries).*—Appearance: Scale-like; margins, papery. Quantity per inflorescence: About 50. Length: About 4 mm. Width: About 1 mm. Shape: Elliptic. Apex: Broadly acute. Base: Truncate. Margin: Entire. Texture, upper and lower surfaces: Glabrous, smooth. Color: Upper surface: 157A. Lower surface: 144C.

*Peduncle.*—Strength: Moderately strong; wiry. Aspect: Upright to about 30° from vertical. Length: About 14 cm. Diameter: About 2 mm. Texture: Smooth, glabrous. Color: 144C.

*Reproductive organs.*—Androecium: Present on disc florets only. Quantity per floret: Five fused around style. Anther shape: Ovoid. Anther length: Less than 1 mm. Anther color: 7A. Amount of pollen: Scarce.

Pollen color: 7A. Gynoecium: Quantity per floret: One. Pistil length: About 6 mm. Stigma shape: Two-parted. Stigma color: 9A. Style length: About 3 mm. Style color: 157A. Ovary color: 157A. Seed/fruit: Seed and fruit production has not been observed.

Disease/pest resistance: Resistance to pathogens and pests common to Argyranthemums has not been observed on plants grown under commercial conditions.

Temperature/weather tolerance: Plants of the new Argyranthemum have been observed to be tolerant to rain, wind and to temperatures from −1 to 30° C.

It is claimed:

1. A new and distinct cultivar of Argyranthemum plant named 'Suparosa', as illustrated and described.

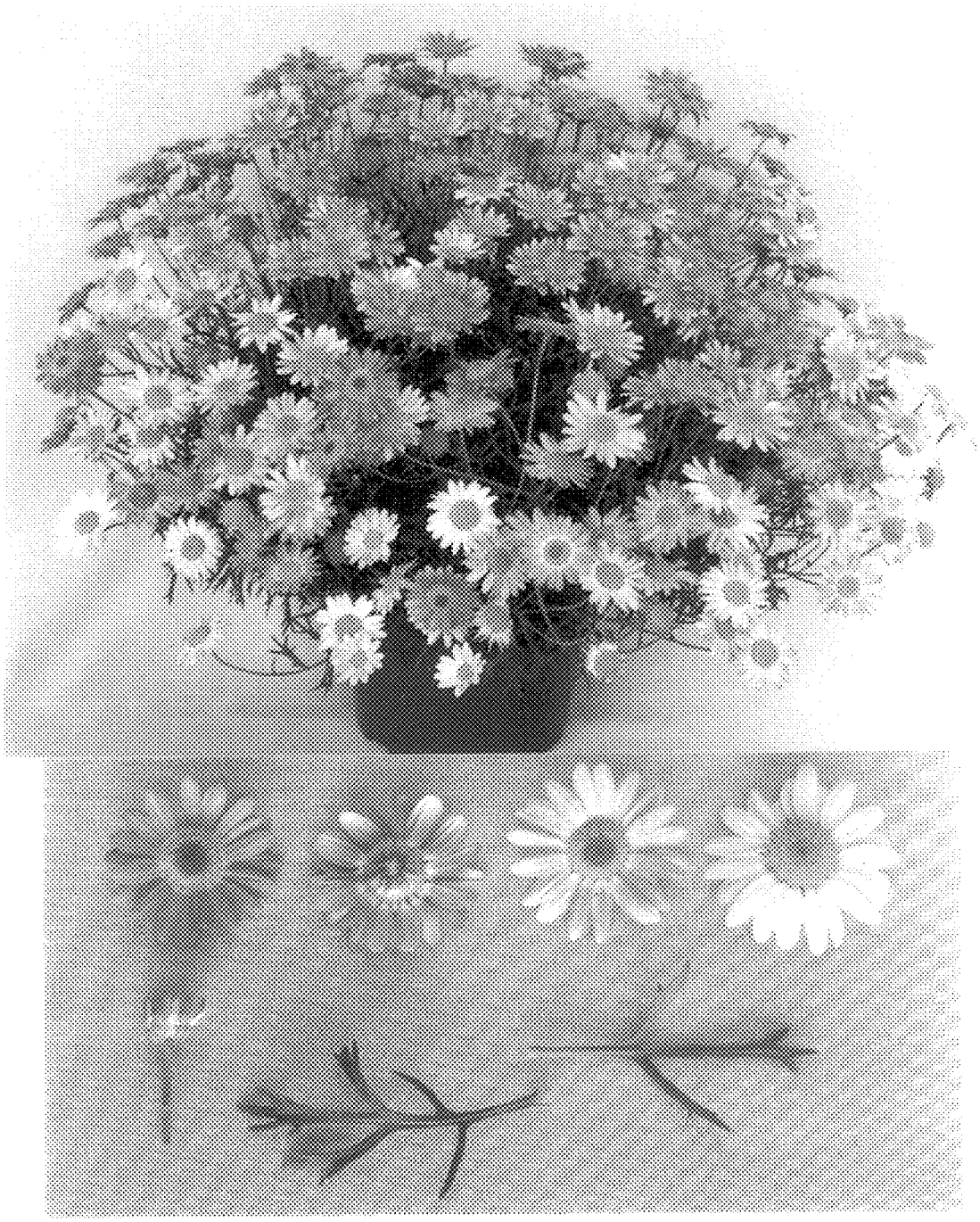

* * * * *